(12) United States Patent
Li

(10) Patent No.: US 8,472,026 B2
(45) Date of Patent: Jun. 25, 2013

(54) COMPACT SURFACE PLASMON RESONANCE APPARATUS AND METHOD

(76) Inventor: Chian Chiu Li, San Jose, CA (US)

( * ) Notice: Subject to any disclaimer, the term of this patent is extended or adjusted under 35 U.S.C. 154(b) by 391 days.

(21) Appl. No.: 12/820,144

(22) Filed: Jun. 22, 2010

(65) Prior Publication Data

US 2011/0310394 A1    Dec. 22, 2011

(51) Int. Cl.
*G01B 9/02* (2006.01)
*G01N 21/55* (2006.01)

(52) U.S. Cl.
USPC .......................................... 356/450; 356/445

(58) Field of Classification Search
USPC .......................................... 356/445, 450, 517
See application file for complete search history.

(56) References Cited

U.S. PATENT DOCUMENTS

| | | | |
|---|---|---|---|
| 6,191,847 B1* | 2/2001 | Melendez et al. | 356/73 |
| 6,862,398 B2* | 3/2005 | Elkind et al. | 356/445 |
| 7,365,855 B2* | 4/2008 | Ho et al. | 356/450 |
| 7,880,891 B1* | 2/2011 | Kim | 356/457 |
| 2007/0146718 A1* | 6/2007 | Takase et al. | 356/445 |
| 2009/0213384 A1* | 8/2009 | Naya et al. | 356/450 |
| 2010/0248352 A1* | 9/2010 | Song et al. | 435/288.7 |

* cited by examiner

Primary Examiner — Michael A Lyons

(57) ABSTRACT

A miniaturized surface plasmon resonance (SPR) sensor is introduced for on-chip applications. The sensor's sensing surface is arranged in between a light source and detector. The structure facilitates building a SPR device on a chip. In one embodiment, a prism and light source are placed on top of a detector chip. In another embodiment, a self-mixing interferometer is incorporated to enable highly sensitive phase measurement. Other embodiments include SPR systems with integrated optical power monitors or on-chip microfluidic SPR systems.

20 Claims, 6 Drawing Sheets

Figure 6:
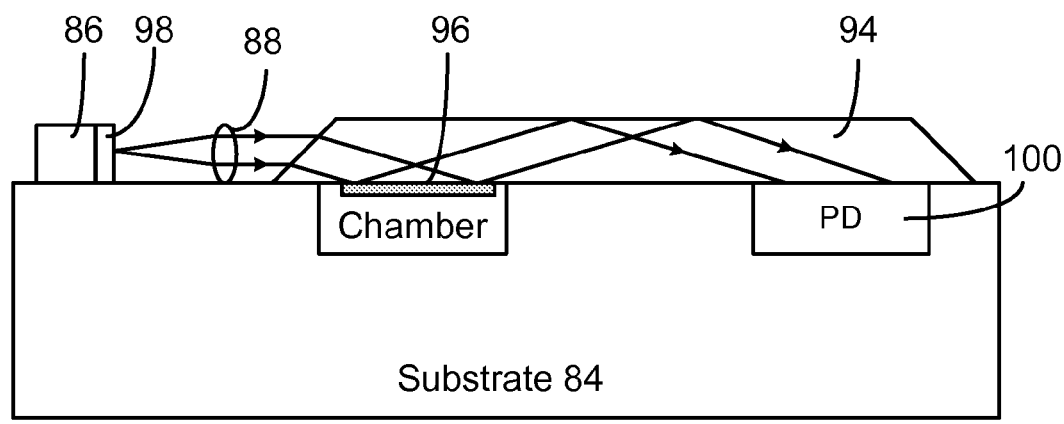

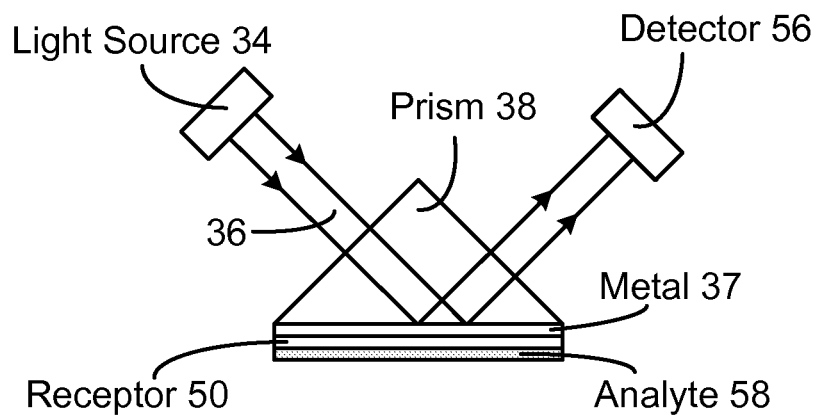
FIG. 1-A (Prior Art)
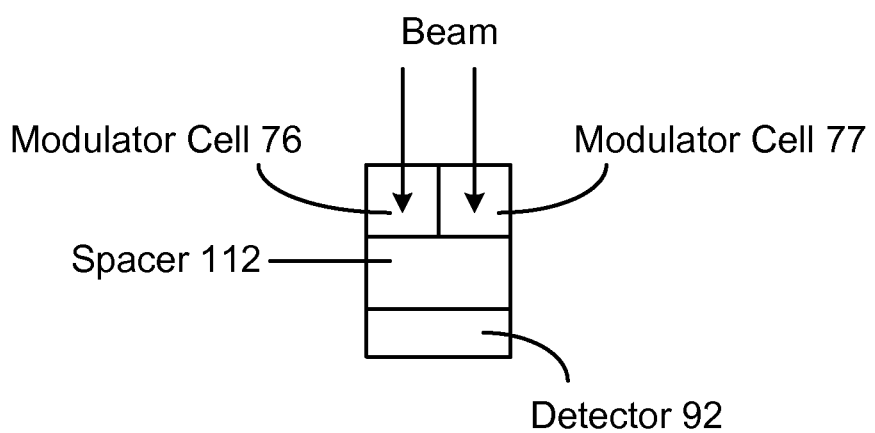
FIG. 1-B (Prior Art)

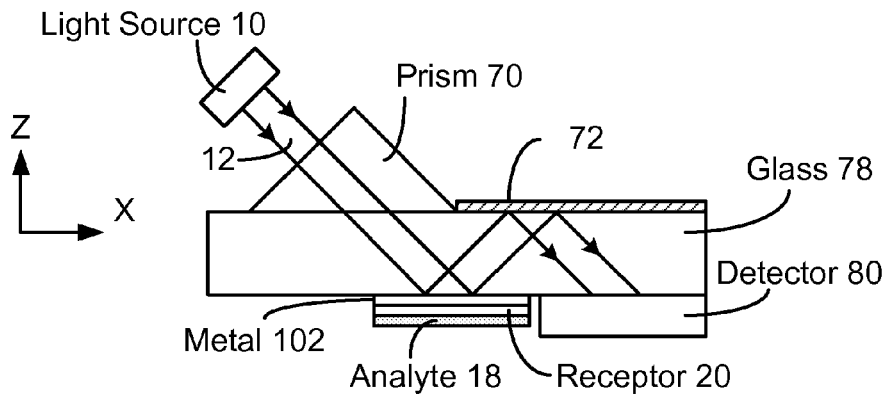
FIG. 2-A
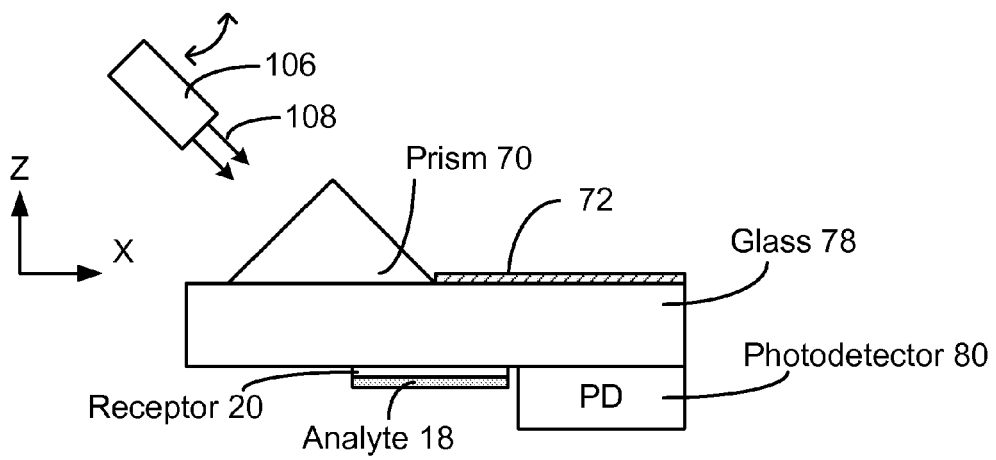
FIG. 2-B
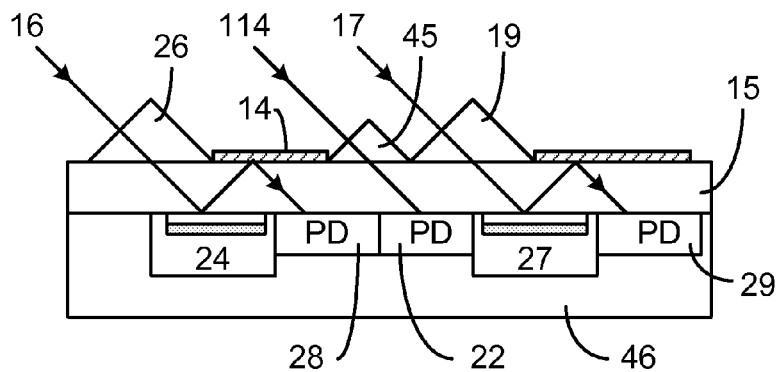
FIG. 2-C

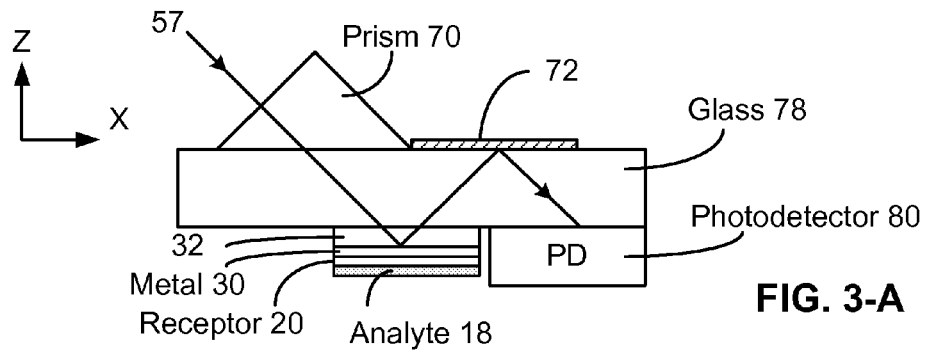
FIG. 3-A
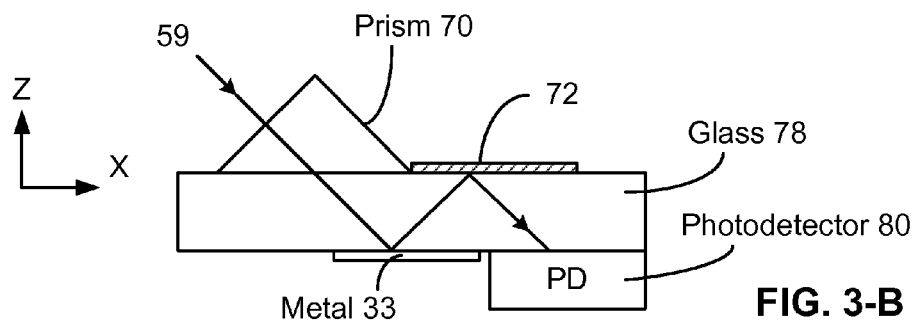
FIG. 3-B
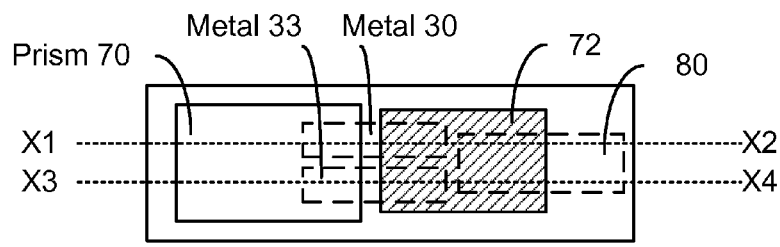
FIG. 3-C
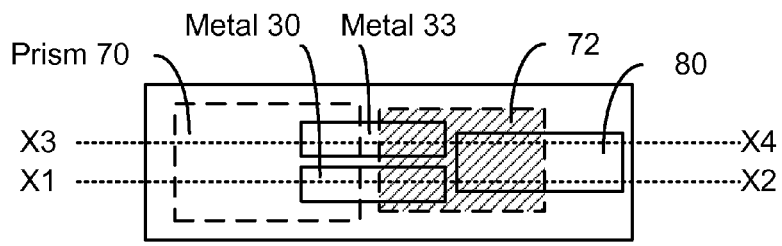
FIG. 3-D

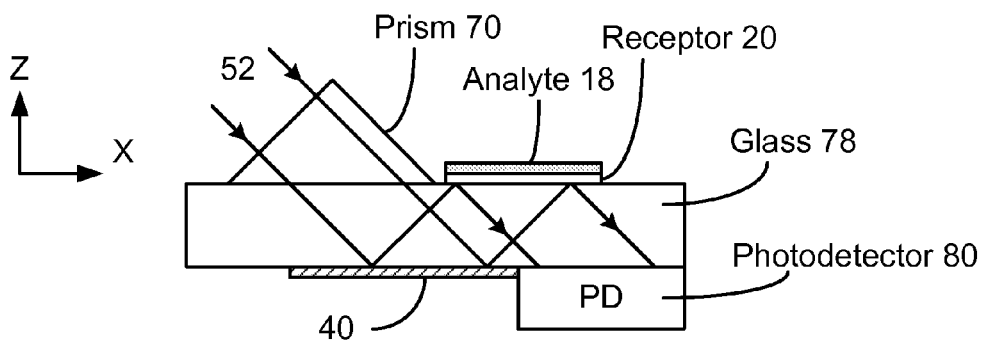
FIG. 4-A
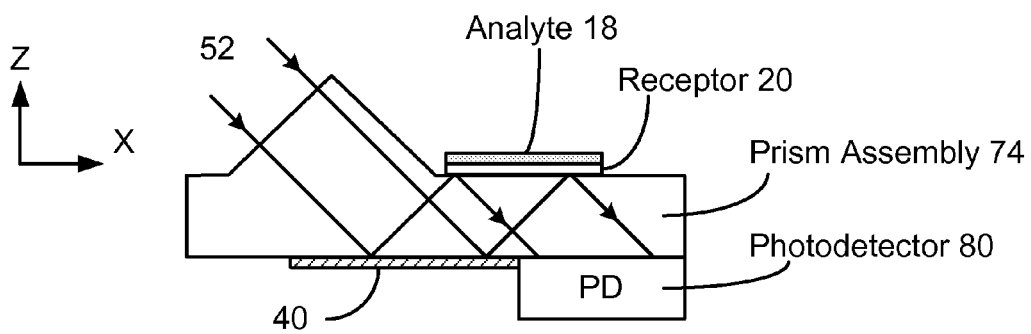
FIG. 4-B
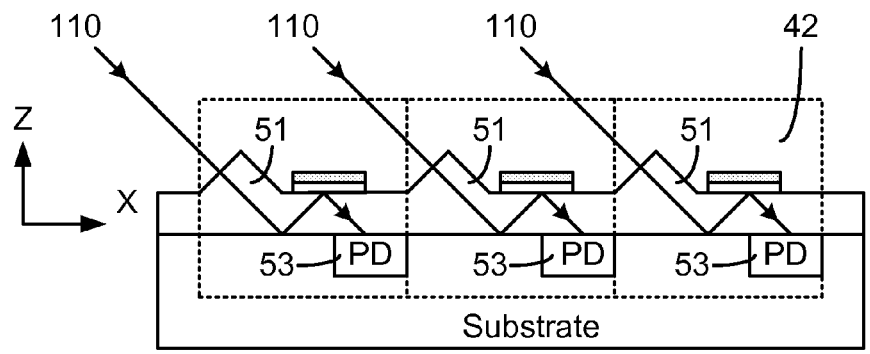
FIG. 4-C

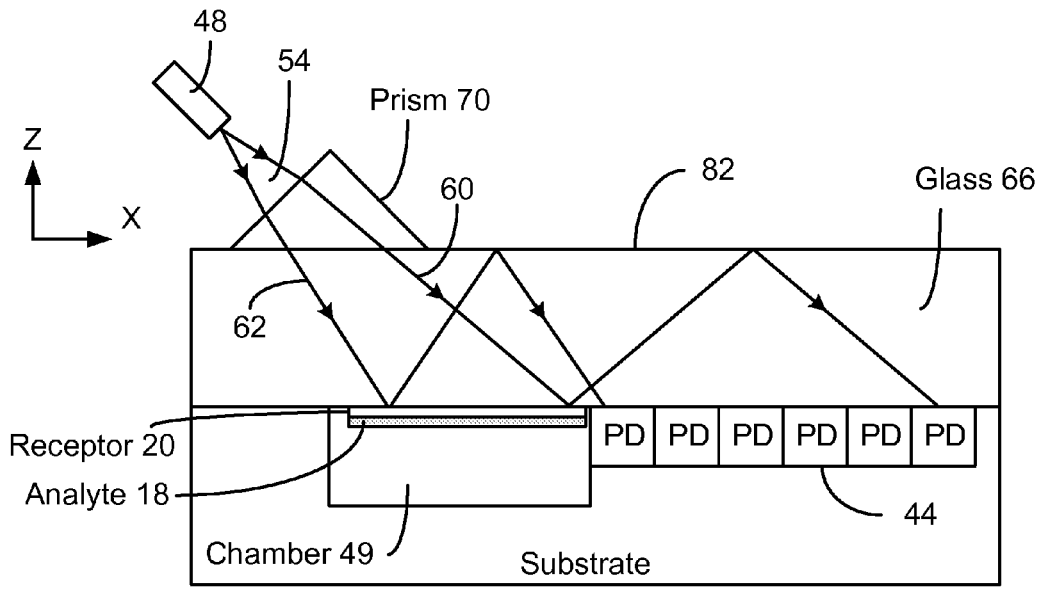
FIG. 5-A
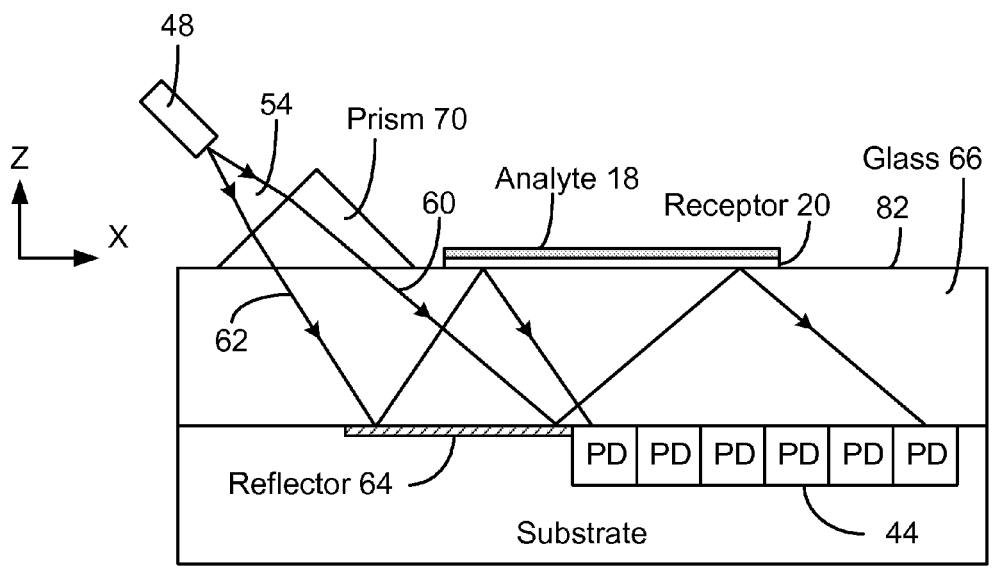
FIG. 5-B

COMPACT SURFACE PLASMON RESONANCE APPARATUS AND METHOD

FEDERALLY SPONSORED RESEARCH

Not applicable

SEQUENCE LISTING OR PROGRAM

Not applicable

BACKGROUND

1. Field of Invention

This invention relates to surface plasmon resonance (SPR) sensors, and particularly to miniaturized SPR sensors suitable for on-chip applications.

2. Description of Prior Art

SPR is a real-time label-free monitoring technology for bio molecules and cells and a great deal of studies have been carried out. SPR systems are widely used at university and government laboratories, clinics, pharmaceutical industries, and homeland security. The principles of SPR are based on the interaction between light (the p-polarized light) and free electrons on a thin metal film. The change of SPR signals reflects change of the refractive index of dielectric medium on the metal film surface. A traditional bulk SPR system contains discrete large-size components and is clumsy and expensive. Its physical size and especially price tag limit the range of use and applications. Melendez, et al. taught a compact SPR device in U.S. Pat. No. 5,912,456. This prior-art SPR is not expensive and has a small size, but its configuration makes it hard for on-chip applications. Besides, its resolution is not competitive to the bulk SPR systems.

Additionally, the emerging lab-on-a-chip (LOC) and micro total analysis system (µTAS) also call for inexpensive on-chip SPR solutions which are compatible with other on-chip devices or microfluidic systems.

Therefore, there exists a need for a high-resolution SPR device that is economic, miniaturized, and compatible with on-chip applications

OBJECTS AND ADVANTAGES

Accordingly, several main objects and advantages of the present invention are:

a). to provide an improved SPR sensor;

b). to provide such a sensor whose sensing surface is arranged between a light source and detector;

c). to provide such a sensor which incorporates a self-mixing interferometer for phase sensitive measurement;

d). to provide such a sensor where at least a prism and detector are integrated; and e). to provide such a sensor which is on-chip, inexpensive, easy to use, and has high resolution.

Further objects and advantages will become apparent from a consideration of the drawings and ensuing description.

SUMMARY

In accordance with the present invention, a miniature SPR sensor is introduced. The sensor is built on a chip and easy to integrate with other on-chip devices. One embodiment employs self-mixing interferometer for highly sensitive phase measurement. With a small footprint, economic price, high resolution, it satisfies the need for biomedical and biochemical research at universities and institutions, medical diagnostics at clinics, drug development at pharmaceutical industry, and chemical and biological monitoring for security and food safety.

Abbreviations

| | |
|---|---|
| AR | Anti-reflection |
| LOC | Lab-on-a-chip |
| PD | Photodetector |
| SPR | Surface plasmon resonance |
| µTAS | Micro total analysis system |

DRAWING FIGURES

FIGS. 1-A and 1-B show respectively a prior-art SPR device and prior-art self-mixing interferometer having integrated photodetector (PD).

FIGS. 2-A to 2-C are schematic cross-sectional views showing respectively embodiments of SPR sensor having wavelength or intensity mode, SPR sensor having angle mode, and SPR sensor array according to the invention.

FIGS. 3-A and 3-B are schematic cross-sectional views showing respectively an interferometric SPR sensor according to the invention.

FIGS. 3-C and 3-D are schematic top and bottom views showing embodiment of the interferometric SPR sensor according to the invention.

FIGS. 4-A to 4-C are schematic cross-sectional views showing respectively embodiments of SPR sensor and SPR sensor array according to the invention.

FIGS. 5-A and 5-B are schematic cross-sectional views showing SPR sensors with angle mode according to the invention.

FIG. 6 is a schematic cross-sectional view depicting an embodiment of SPR sensor that integrates light source, prism, and detector according to the invention.

REFERENCE NUMERALS IN DRAWINGS

| | | | |
|---|---|---|---|
| 10 | Light source | 12 | Beam |
| 14 | Reflector | 15 | Glass |
| 16 | Beam | 17 | Beam |
| 18 | Analyte | 19 | Prism |
| 20 | Receptor | 22 | Detector |
| 24 | Chamber | 26 | Prism |
| 27 | Chamber | 28 | Detector |
| 29 | Detector | 30 | Metal film |
| 32 | Layer | 33 | Metal film |
| 34 | Light source | 36 | Beam |
| 37 | Metal film | 38 | Prism |
| 40 | Metal film | 42 | SPR unit |
| 44 | Detector | 45 | Prism |
| 46 | Substrate | 48 | Light source |
| 49 | Chamber | 50 | Receptor |
| 51 | Prism | 52 | Beam |
| 53 | PD | 54 | Beam |
| 56 | Detector | 57 | Beam |
| 58 | Analyte | 59 | Beam |
| 60 | Beam | 62 | Beam |
| 64 | Reflector | 66 | Glass |
| 70 | Prism | 72 | Reflector |
| 74 | Prism assembly | 76 | Modulator cell |
| 77 | Modulator cell | 78 | Glass |
| 80 | Detector | 82 | Surface |
| 84 | Substrate | 86 | Submount |
| 88 | Lens system | 92 | Detector |
| 94 | Prism | 96 | Metal film |
| 98 | Light source | 100 | Detector |

-continued

| 102 | Metal | 106 | Light source |
| 108 | Beam | 110 | Beam |
| 112 | Spacer | 114 | Beam |

DETAILED DESCRIPTION—FIGS 1-A AND 1-B—PRIOR-ART

FIG. 1-A shows a cross-sectional view of prior-art SPR system. A collimated beam 36 from a light source 34 is directed to enter a prism 38. Beam 36 undergoes the attenuated total internal reflection at the bottom of the prism. A detector 56 is placed to measure the reflected light. On the prism bottom, a metal film 37 is deposited to facilitate the SPR effect. A bio molecular receptor layer 50 is adsorbed on film 37 for the purpose to bind analyte molecules 58 through the specific binding. Once analyte 58 is attached to receptor layer 50, it causes change of refractive index in the proximity of metal film 37. The index change in turn changes the condition of SPR phenomena. Therefore, the binding of analyte 58 can be detected by the SPR signals received by detector 56. The prior-art SPR system includes multiple stand-alone bulk devices, making it expensive and clumsy.

FIG. 1-B shows a cross-sectional view of prior-art self-mixing optical interferometer. An incident beam is transmitted to impinge on a spatial phase modulator and passes through modulator cells 76 and 77 respectively. The modulator cells have a dimension smaller than the wavelength along a direction perpendicular to the beam propagation. Cells 76 and 77 divide the incident beam by wavefront division to create two beam portions whose width is smaller than the wavelength. Due to diffraction, beam expansion happens after the beam portions pass through and come out of the modulator cells. Beam spreading and small beam spacing together cause the beam portions to mix and interfere with each other in a spacer region 112. As a result, a detector 92 can be disposed in a substantial short distance to the modulator cells to measure interference signals. Therefore, a focus lens, which is required for a conventional free-space interferometer, is no longer needed for mixing the beams and the interferometer can be made ultra-compact and on a chip.

FIGS. 2-A to 2-C Embodiments of SPR Sensors

FIG. 2-A shows schematically a compact SPR embodiment in a cross-sectional view in x-z plane. The SPR system comprises a light source 10, a prism assembly containing a prism 70 and a glass block 78, a reflector 72, and a PD 80. A collimated probe beam 12 from light source 10 is transmitted to enter prism 70, glass 78 and then reflected by the bottom of the glass where a thin metal film 102 is deposited. On the surface of metal film 102, a receptor layer 20 is adsorbed, which is used to catch analyte molecules 18. Next, the beam is reflected again by reflector 72 and received by PD 80.

Principles of the SPR of FIG. 2-A are the same as a conventional SPR in that analyte information is collected during the attenuated total internal reflection of light at a thin metal layer region where activities of plasmon is involved. But the structure here is more compact than the prior-art SPR. It is also easy to make. As light source 10 and PD 80 are on the opposite sides of metal film 102, integration becomes more convenient. For example, the detector can be attached to the prism assembly, or a prism can be arranged on the surface a detector.

As a conventional SPR, analyte 18 may be measured by monitoring beam intensity while wavelength or incident angle relative to the glass block or metal film is changed, as well known in the field. The latter case is shown graphically in FIG. 2-B, where a light source 106 is rotated around the y-axis, causing change of the incident angle of a probe beam 108. Analyte 18 can also be detected through tracking the beam intensity while maintaining the wavelength. Change of the intensity indicates either the analyte is adsorbed or washed away.

The SPR scheme shown in FIG. 2-A can be easily adapted to make a SPR array as depicted exemplarily in FIG. 2-C. The array embodiment comprises a prism 26, PD 28, reflector 14, and test chamber 24 for a SPR unit as well as a prism 45 and PD 22 for power monitoring. The PD array is fabricated on a substrate 46. A probe beam is split by wavefront division into multiple beam portions including 16 and 114, which are used for SPR sensing and power calibration respectively. Also shown is another SPR unit consisting of a prism 19, PD 29, and chamber 27, where a beam portion 17 is involved. Bio samples are measured at the test chamber which may be connected to a microfluidic system. The prisms and a transparent block 15 beneath them can be made a single piece by molding method and the molded piece and the PD array can be bonded together. The molding materials may be of glass or polymer.

Monitor PD 22 measures directly power intensity, which can be used to calibrate SPR results. An array of power monitors may also be placed among the SPR units. When high precision input power is available, assuming the wavelength is stable, SPR signals can be obtained by monitoring beam intensity change during the analyte-receptor binding process, which overcomes the measurement difficulties caused by power drifting of a light source.

In addition, multiple SPR units can be used for differential measurement. As in FIG. 2-C, chambers 24 and 27 may contain a reference and sample medium. The SPR units share the same light source and have the same structure. Thus differential method can be employed to cancel the light source noise. The scheme works to counter errors caused by wavelength shift as well, where the effect is felt simultaneously.

FIGS. 3-A to 3-D Embodiments of Interferometric SPR Sensor

FIGS. 3-A to 3-D show schematically a SPR embodiment performing interferometric phase measurement. As is well known, a SPR process can be monitored with high sensitivity by measuring the phase change. FIG. 3-A is a cross-sectional view in x-z plane which is similar to the one in FIG. 2-A except a spacer layer 32 is inserted between a metal film 30 and glass 78. Layer 32 is used to adjust the phase of a beam 57. FIG. 3-B shows another cross-sectional view of the embodiment where there is no spacer layer between glass 80 and a metal film 33 and there is no acceptor layer, either. Thus a beam 59 of FIG. 3-B is phase delayed less than beam 57 of FIG. 3-A.

The views of FIGS. 3-A and 3-B are along lines X1-X2 and X3-X4 in FIGS. 3-C and D respectively, which are a top and bottom view of the device when looking in the z direction. The system contains two side-by-side sub-structures. Beams 57 and 59 belong to one probe beam and they are separated after being reflected by metal films 30 and 33 respectively. Spacer layer 32 is designed such that beam 57 is phase delayed relative to beam 59 by a predetermined value, e.g. half of pi. The dimensions of films 30 and 33 along y-axis is arranged to be smaller than the wavelength of the probe beam. Then after the reflection, there are two beams whose width is smaller than the wavelength in y direction. The two beams merge by themselves and interfere with each other on the way to a reflector 72 and PD 80. The interference signals can indicate tiny change of the refractive index caused by the analyte.

Similarly, we can build another SPR unit close by (not shown) which has exactly the same structure but no analyte introduced to perform differential measurement. Subtraction between the interference signals, one influenced by the analyte while the other is not, yields even higher sensitivity, because it cancels noise from the light source and environment.

FIGS. 4-A to 4-C, 5-A, 5-B, and 6 Embodiments of SPR Sensors

FIG. 4-A shows an embodiment of another compact SPR sensor in a cross-sectional view. The scheme is similar to the one in FIG. 2-A but differs from it in that a receptor layer and prism are placed on the same side of the glass block. A probe beam 52 is reflected by a reflector 40 after passing prism 70 and glass 78. The beam then is bounced again by the attenuated total internal reflection. It interacts with a metal film (not shown) and collects information of the analyte before reaching PD 80. As mentioned before, the prism and glass sheet can be made by molding into one piece, as a prism assembly 74 shown in FIG. 4-B. The molding material may be of a type of transmissive polymer or glass. Molding also works for a SPR array as illustrated graphically in FIG. 4-C. The molded part contains multiple SPR units 42. Each unit comprises a prism assembly 51 and PD 53. A probe beam is split into multiple beams 110 which impinge onto the SPR units respectively. The system may be made by boding a molded part with a PD array. One merit of the embodiments of FIGS. 4-A to 4-C is that a chamber and detector are disposed in different layer sections. As a result, a detector can occupy a whole layer, making selection of a detector less restricted. For example, off-the-shelf photo detectors like CCD and CMOS sensing chips can be used. A prism assembly along with microfluidic channels can be fabricated on or bonded to the CCD or CMOS surface.

Shown schematically in FIGS. 5-A and 5-B are embodiments of compact SPR sensor using angle mode measurement without rotating a beam. In FIG. 5-A, a cross-sectional view in x-z plane, a light source 48 emits a probe beam 54. The beam is divergent in x-z plane. First the beam passes through a prism 70 and a glass block 66, and then it is reflected by the bottom surface of block 66 where a thin metal film (not shown) is coated. As a regular SPR, there are receptor layer 20 and analyte 18 adsorbed on the metal film in a chamber 49. After reflection the beam is transmitted to a top surface 82 of the glass. If the ambience is of vacuum or air, the total internal reflection happens at the surface. A reflector can also be placed on surface 82 when needed. After the second reflection, the beam is transmitted to a PD array 44.

Because beam 60 is divergent, when it impinges on the block's bottom surface, different parts of the beam have different incident angles. In FIG. 5-A, for example, sub-beams 60 and 62 have different incident angles and follow their own paths to reach different units of PD array 44 respectively. Thus the configuration produces results representing SPR effect at various beam incident angles. It enables angle mode of SPR test without a moving part to adjust the angle of beam 54.

FIG. 5-B depicts a similar setup as that in FIG. 5-A, except that the adsorption region is arranged on the top surface of block 66 and a reflector 64 is deposited on the bottom surface. This scheme provides another angle-mode structure which may have a prism, glass block, and test chamber or channel molded in a single glass or polymer piece. The schemes in FIGS. 5-A and 5-B can be made more compact by attaching the light source directly on prism 70.

An integrated SPR scheme is described schematically in FIG. 6, where all components are arranged on a chip, i.e., based on a substrate 84. Attached on the substrate surface are a light source 98, submount 86, lens system 88, and prism 94. Beneath prism 94 are a test chamber and a PD 100. A medal film 96 is arranged on the prism bottom and inside the test chamber. A beam is arranged to enter prism 94 and to impinge on the bottom surface of the prism at an angle that supports the SPR effect. Then the beam is reflected by the prism top and directed to PD 100.

Conclusion, Ramifications, And Scope

Thus it can be seen that a SPR sensor can be miniaturized by arranging a light source and detector on the opposite sides of a SPR sensing film and integrating the components.

The miniature sensor has the following advantages: High resolution, compactness, low cost, and compatibility with other on-chip devices.

Although the description above contains many specificities, these should not be construed as limiting the scope of the invention but as merely providing illustrations of some of the presently preferred embodiments. Numerous modifications will be obvious to those skilled in the art.

Ramifications:

It is noted that the abovementioned SPR methods can be combined to create new structures. For example, the phase mode scheme of FIGS. 3-A to 3-D can be combined with the array idea of FIG. 2-C or 4-C. The reflectors 72, 40, 64 may become unnecessary when the glass surface enables the total internal reflection. Different modes of measurements can also be combined to enhance resolution and reliability. AR coating may be deposited on certain surfaces of prism and PD to reduce optical power loss. And a data collection and processing integrated circuit may be fabricated on the same substrate of a PD using semiconductor technologies. A glass block of SPR system can be replaced by a transmissive polymer block.

Lastly, a wavelength tunable light source can be employed for wavelength mode SPR detection for the embodiments discussed.

Therefore the scope of the invention should be determined by the appended claims and their legal equivalents, rather than by the examples given.

The invention claimed is:

1. An optical apparatus comprising:
   1) an optical body adapted in operation for mounting a measurement area comprising a material which is capable of supporting plasmonic phenomenon;
   2) a light source for providing a first beam, said first beam arranged for generating said plasmonic phenomenon in said measurement area and producing a second beam;
   3) said apparatus arranged such that said plasmonic phenomenon affects said second beam; and
   4) a detector for measuring said second beam, said detector arranged such that said detector is positioned in substantial proximity to a plane which said measurement area overlaps, said apparatus arranged such that said plane is in between said light source and said detector or said plane overlaps said detector.

2. The apparatus according to claim 1 wherein at least two of the following items are integrated together: said light source, said optical body, and said detector.

3. The apparatus according to claim 1 wherein said detector includes a detector array.

4. The apparatus according to claim 1 wherein said first beam is split into a plurality of beam portions for performing a plurality of measurements, said beam portions being spaced apart.

5. The apparatus according to claim 1, further including differential means for performing differential measurements.

6. The apparatus according to claim 1, further including interference means for performing measurements using interference and phase difference.

7. The apparatus according to claim 1, further including fluidic means for transporting a sample under test by fluidic media.

8. An optical apparatus comprising:
   1) an optical body adapted in operation for mounting a measurement area comprising a material which is capable of supporting plasmonic phenomenon;
   2) a light source for providing a first beam, said first beam being collimated, said first beam arranged for generating said plasmonic phenomenon in said measurement area and producing a second beam;
   3) said apparatus arranged such that said plasmonic phenomenon affects said second beam; and
   4) a detector for measuring said second beam, said apparatus arranged such that said detector and said optical body are integrated and said detector is positioned within a 20 millimeter distance to a plane which said measurement area overlaps.

9. The apparatus according to claim 8 wherein said light source and said optical body are integrated.

10. The apparatus according to claim 8 wherein said detector includes a detector array.

11. The apparatus according to claim 8 wherein said first beam is split into a plurality of beam portions for performing a plurality of measurements, said beam portions being spaced apart.

12. The apparatus according to claim 8, further including differential means for performing differential measurements.

13. The apparatus according to claim 8, further including interference means for performing measurements using interference method.

14. The apparatus according to claim 8, further including fluidic means for transporting a sample under test by fluidic media.

15. An optical apparatus comprising:
   1) an optical body adapted in operation for mounting a measurement area comprising a material which is capable of supporting plasmonic phenomenon;
   2) a light source for providing a first beam with radiation capable of generating said plasmonic phenomenon;
   3) interference means for splitting said first beam by wavefront division, producing a first and a second beam portion, and mixing said first and second beam portions for generating interference;
   4) said apparatus arranged such that said plasmonic phenomenon affects at least one of said first and second beam portions; and
   5) a detector for measuring said interference.

16. The apparatus according to claim 15 wherein at least two of the following items are integrated together: said light source, said optical body, and said detector.

17. The apparatus according to claim 15 wherein said detector includes a detector array.

18. The apparatus according to claim 15 wherein said interference means is arranged such that the beam width of at least one of said first and second beam portions is smaller than its wavelength.

19. The apparatus according to claim 15, further including differential means for performing differential measurements.

20. The apparatus according to claim 15, further including fluidic means for transporting a sample under test by fluidic media.

* * * * *